(12) United States Patent
Stolle et al.

(10) Patent No.: US 6,433,004 B1
(45) Date of Patent: Aug. 13, 2002

(54) SUBSTITUTED β,γ-ANELLATED LACTONES

(75) Inventors: Andreas Stolle, Milford, CT (US);
Horst-Peter Antonicek, Bergisch Gladbach (DE); Stephen Lensky, Kürten (DE); Arnd Voerste, Köln (DE); Thomas Müller, Bonn-Beuel (DE); Jörg Baumgarten, Wuppertal (DE); Karsten von dem Bruch; Gerhard Müller, both of Leverkusen (DE); Udo Stropp, Haan (DE); Ervin Horváth, Leverkusen (DE); Jean-Marie-Viktor de Vry, Rösrath (DE); Rudy Schreiber, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/600,430

(22) PCT Filed: Jan. 5, 1999

(86) PCT No.: PCT/EP99/00022
§ 371 (c)(1),
(2), (4) Date: Jul. 14, 2000

(87) PCT Pub. No.: WO99/36417
PCT Pub. Date: Jul. 22, 1999

(30) Foreign Application Priority Data

Jan. 17, 1998 (DE) .......................................... 198 01 647

(51) Int. Cl.⁷ ..................... A61K 31/381; C07D 307/83; C07D 307/935; C07D 333/56; C07D 407/04
(52) U.S. Cl. ....................... 514/443; 514/444; 514/468; 514/470; 549/58; 549/301; 549/307; 549/312
(58) Field of Search ................................ 514/443, 444, 514/468, 470; 549/58, 301, 307, 312

(56) References Cited

U.S. PATENT DOCUMENTS

| 5,688,826 A | 11/1997 | Massey et al. ............... 514/433 |
| 5,843,988 A | 12/1998 | Annoura et al. ............. 514/454 |

FOREIGN PATENT DOCUMENTS

| EP | 0656345 | 6/1995 | ......... C07C/229/36 |
| EP | 0658539 | 6/1995 | ......... C07C/229/24 |
| EP | 0774454 | 5/1997 | ......... C07C/229/50 |
| EP | 0774461 | 5/1997 | ......... C07D/209/52 |
| JP | 49110659 | * 10/1974 | |
| WO | 9210583 | 6/1992 | ......... C12P/21/06 |
| WO | 9515940 | 6/1995 | ......... C07C/229/24 |
| WO | 9515941 | 6/1995 | ......... C07C/229/36 |
| WO | 9525110 | 9/1995 | ......... C07D/513/02 |
| WO | 9605818 | 2/1996 | ......... A61K/31/135 |
| WO | 9607405 | 3/1996 | ......... A61K/31/19 |
| WO | 9615099 | 5/1996 | ......... C07C/229/46 |
| WO | 9615100 | 5/1996 | ......... C07C/229/46 |
| WO | 9701790 | 1/1997 | ......... G02F/1/1337 |
| WO | 9705109 | 2/1997 | ......... C07D/209/18 |
| WO | 9705137 | 2/1997 | ......... C07D/473/04 |

OTHER PUBLICATIONS

Bando, T.; Tanaka, S.; Fugami, K.; Yoshida, Z.; Tamaru, Y.; "Efficient Systhesis of 2–Vinyl–γ–butyrolactones and 2–Vinyl–γ–butyrolactams by Paladium–Catalyzed Decarboxylative Carbonylation ", Bull. Chem. Soc. Jpn. 65:97–110 (1992).

Kelly, H. A.; Bolton, R.; Brown, S. A.; Coote, S. J.; Dowle, M.; Dyer, U.; Finch, H.; Golding, D.; Lowdon A.; McLaren, J.; Montana, J. G.; Owen, M. R.; Pegg, N. A.; Ross, B. C.; Thomas, R.; and Walker, D. A., "Synthesis of Tran–Fused [5,5] Bicyclic Lactones / Lactams as Templates for Serine Protease Inhibition", Tetrahedron Letters 39,(38): 6979–6982 (1998).

Smith, A. B.; and Richmond, R. E., "Total Synthesis of the Paniculides ", J. Am. Chem. Soc. 105: 575–585 (1983).

Chavis, P., Nooney, J. M., Bockaert, J., Fagni, L., Feltz, A., and J. L. Bossu, "Facilitatory Coupling between a Glutamate Metabotropic Receptor and Dihydropyridine–Sensitive Calcium Channels in Cultured Cerebellar Granule Cells", J. Neurosci., 15(1): 135–143 (Jan. 1995).

Chavis, P., Shinozaki, H., Bockaert, J., and Fagni, L., "The Metabotropic Glutamate Receptor Types 2/3 Inhibit L–Type Calcium Channels via a Pertussis Toxin–Sensitive G–Protein in Cultured Cerebellar Granule Cells", J. Neurosci., 14(11): 7067–7076 (Nov. 1994).

Conn, J. P., and Pin, J.–P., "Phamacology and Functions of Metabotropic Glutamate Receptors", Annu. Rev. Pharmacol. Toxicol., 37: 205–237 (1997).

* cited by examiner

Primary Examiner—T. A. Solola

(57) ABSTRACT

The present invention relates to novel substituted β,γ-fused lactones, to processes for their preparation and to their use for the prevention and/or treatment of disorders caused by hyper- or hypofunction of the glutamatergic system, in particular of cerebral ischaemias, craniocerebral trauma, states of pain or CNS-mediated spasms.

10 Claims, No Drawings

SUBSTITUTED β,γ-ANELLATED LACTONES

This application is a 371 of PCT/EP99/00022 field Jan. 5, 1999.

The present invention relates to β,γ-fused lactones, to processes for their preparation and to their use as pharmaceuticals.

The amino acid L-glutamate is the most important excitatory neurotransmitter in the brain. Glutamate receptors can be divided into into two major classes: 1. ionotropic receptors which control the ion channels directly and 2. metabotropic receptors (mGluRs).

Metabotropic glutamate receptors are a heterogeneous class of G-protein-coupled receptors. Pre- and postsynaptically, they modulate the release of glutamate and the sensitivity of the cell to glutamate, respectively. The effects are caused via different second-messenger cascades. This response, in turn, has an effect on the ionotropic glutamate receptors.

Presently, 8 different suptypes of metabotropic glutamate receptors are known, differing in the second-messenger cascade, pharmacology and localization in the brain (review in: Ann. Rev. Pharmacol. Toxicol. 1997, 37, 205).

The present invention relates to β,γ-fused lactones of the general formula (I)

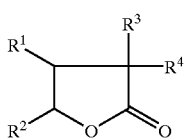

(I)

in which
R¹ and R² together represent radicals of the formulae

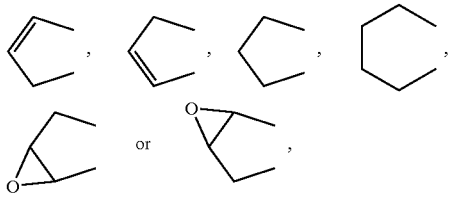

which are optionally substituted up to 3 times by hydroxyl, $R^3$ represents hydrogen, $(C_1-C_6)$-alkyl or represents $(C_2-C_6)$-alkenyl
and
$R^4$ represents a radical of the formula —$CH_2$—$R^5$,
in which
$R^5$ represents aryl having 6 to 10 carbon atoms or benzothiophene which is attached via the heterocycle, where the ring systems are optionally mono- to polysubstituted by identical or different substituents from the group consisting of halogen and $(C_1-C_6)$-alkyl,
or
$R^3$ represents $(C_2-C_6)$-alkenyl
and
$R^4$ represents hydrogen
and their pharmaceutically acceptable salts.

The compounds according to the invention can exist in stereoisomeric forms which either behave as image and mirror image (enantiomers), or which do not behave as image and mirror image (diastereomers). The invention relates both to the enantiomers or diastereomers and their respective mixtures. Like the diastereomers, the racemic forms can be separated into the stereoisomerically uniform components in a known manner.

Physiologically acceptable salts of the compounds according to the invention can be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which can be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiusopropylamine, procaine, dibenzylamine, N-methylmorpholine, dihydroabietylamine, 1-ephenamine or methylpiperidine.

In general, aryl represents an aromatic radical having 6 to 10 carbon atoms. Preferred aryl radicals are phenyl and naphthyl.

In the context of the invention, $(C_1-C_6)$-alkyl represents a straight-chain or branched alkyl radical having 1 to 6 carbon atoms. Preference is given to a straight-chain or branched alkyl radical having 1 to 4 carbon atoms. Examples which may be mentioned are: methyl, ethyl, propyl, isopropyl, tert-butyl, n-pentyl and n-hexyl.

In the context of the invention, $(C_2-C_6)$-alkenyl represents a straight-chain or branched alkenyl radical having 2 to 6 carbon atoms. Preference is given to a straight-chain or branched alkenyl radical having 3 to 5 carbon atoms. Examples which may be mentioned are: vinyl, allyl, isopropenyl, but-3-en-1-yl, n-pent-3-en-1-yl and n-hex-3-en-1-yl.

Preference is given to compounds of the general formula (I) according to the invention in which
$R^1$ and $R^2$ together represent radicals of the formulae

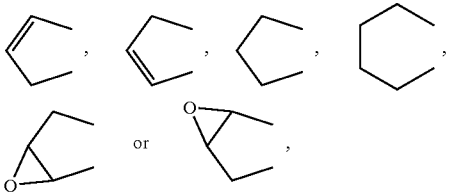

which are optionally substituted up to 3 times by hydroxyl,
$R^3$ represents hydrogen or represents $(C_2-C_5)$-alkenyl
and
$R^4$ represents a radical of the formula -$CH_2$—$R^5$,
in which
$R^5$ represents phenyl, naphthyl or benzothiophene which is attached via the heterocycle, where the ring systems are optionally mono- to polysubstituted by identical or different substituents from the group consisting of fluorine, chlorine, bromine and $(C_1-C_4)$-alkyl,
or
$R^3$ represents $(C_2-C_5)$-alkenyl and R$^4$ represents hydrogen and their pharmaceutically acceptable salts.

Particular preference is given to compounds of the general formula (I) according to the invention, in which R$^1$ and R$^2$ together represent radicals of the formulae

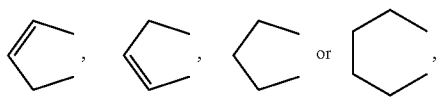

which are optionally substituted up to 2 times by hydroxyl,

R$^3$ represents hydrogen or represents (C$_3$–C$_5$)-alkenyl and

R$^4$ represents a radical of the formula –CH$_2$—R$^5$, in which

R$^5$ represents phenyl, naphthyl or benzothiophene which is attached via the heterocycle, where the ring systems are optionally mono- to disubstituted by identical or different substituents from the group consisting of fluorine, chlorine, bromine and (C$_1$–C$_3$)-alkyl, or R$^3$ represents (C$_3$–C$_5$)-alkenyl and R$^4$ represents hydrogen and their salts.

Very particular preference is given to compounds according to the invention of the following structure:

Structure:

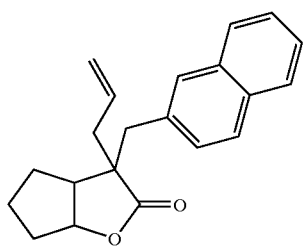

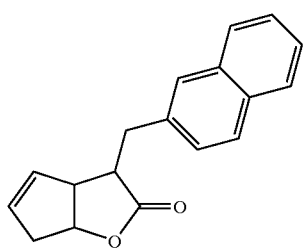

-continued

Structure:

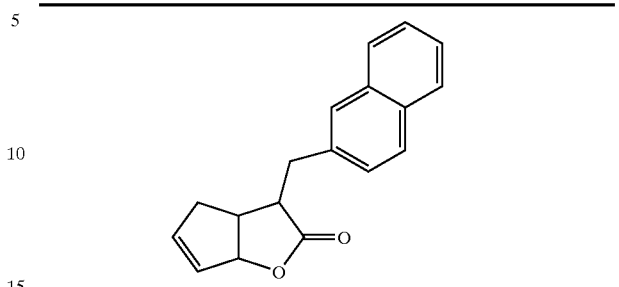

The compounds of the general formula (I) according to the invention can be prepared by

[A] reacting compounds of the general formula (II),

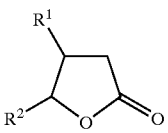
(II)

in which

R$^1$ and R$^2$ are as defined above.

with compounds of the general formula (III)

R$^4$—A  (III)

in which

R$^4$ is as defined above and

A represents halogen, preferably bromine, in inert solvents and in the presence of a base to give the compounds of the general formula (Ia)

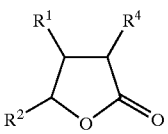
(Ia)

in which

R$^1$, R$^2$ and R$^4$ are as defined above, and, in the case that R$^3$ does not represent hydrogen, reacting the compounds of the general formula (Ia) with compounds of the general formula (IV)

R$^{3'}$—D  (IV)

in which

R$^{3'}$ has the meaning of R$^3$ given above. but does not represent hydrogen.

D represents halogen, preferably bromine, in inert solvents and in the presence of a base, or

[B] initially reacting compounds of the general formula (II) with compounds of the general formula (IV) as described under [A] to give the compounds of the general formula (Ib)

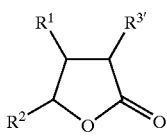

in which

R[1]. R[2] and R[3'] are as defined above, and in a second step with compounds of the general formula (III).

The processes according to the invention can be illustrated in an exemplary manner by the formula scheme below:

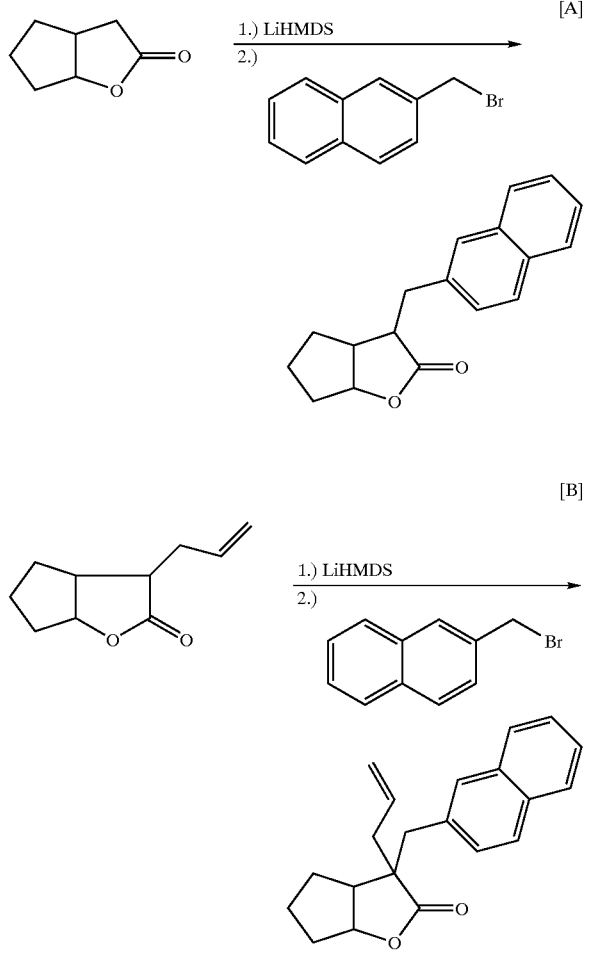

Suitable solvents are all inert solvents which do not change under the reaction conditions. These preferably include ethers, such as diethyl ether, dioxane, tetrahydrofuran, glycol dimethyl ether or diethylene glycol dimethyl ether. Particular preference is given to tetrahydrofuran.

Suitable bases are the customary inorganic or organic bases. These preferably include alkali metal hydroxides, such as, for example, sodium hydroxide, potassium hydroxide, or alkali metal carbonates, such as sodium carbonate or potassium carbonate, or sodium methoxide or potassium methoxide, or sodium ethoxide or potassium ethoxide or potassium tert-butoxide, or amides, such as sodium amide, lithium bis-(trimethylsilyl)amide, lithium diisopropylamide, or organometallic compounds, such as butyllithium or phenyllithium. Preference is given to lithium diisopropylamide and lithium bis-(trimethylsilyl)amide.

Here, the base is employed in an amount of from 1 to 5, preferably from 1 to 2, mol, based on 1 mol of the compounds of the general formulae (III) and (IV).

The reaction is generally carried out in a temperature range of from −78° C. to reflux temperature, preferably from −78° C. to +20° C.

The reaction can be carried out under atmospheric, elevated or under reduced pressure (for example from 0.5 to 5 bar). In general, the reaction is carried out at atmospheric pressure.

The compounds of the general formula (I) according to the invention are suitable for use as medicaments in the treatment of humans and animals.

The compounds of the general formula (I) according to the invention are suitable for modulating metabotropic glutamate receptors and therefore influence the glutamatergic neurotransmitter system.

For the purpose of the invention, a modulator of the metabotropic glutamate receptor is an agonist or antagonist of this receptor.

The compounds according to the invention are particularly suitable as modulators of the metabotropic glutamate receptor of subtype 1, very particularly as antagonists of this receptor subtype.

Owing to their pharmacological properties, the compounds according to the invention can be used, on their own or in combination with other pharmaceuticals, for the treatment and/or prevention of neuronal damage or disorders associated with a decompensation of the physiological or with pathophysiological conditions of the glutamatergic system in the central and peripheral nervous system.

For the treatment and/or prevention of neuronal damage caused, for example, by ischaemic, thromb- and/or thrombemolic, and haemorrhagic stroke, conditions after direct and indirect injuries in the area of the brain and the skull. Furthermore for the treatment and/or prevention of cerebral ischaemias after all surgical interventions in the brain or peripheral organs or body parts and conditions of pathogenic or allergic nature accompanying or preceding them, which can lead primarily and/or secondarily to neuronal damage.

Likewise, the compounds according to the invention are also suitable for the therapy of primary and/or secondary pathological conditions of the brain, for example during or after cerebral vasospasms, hypoxia and/or anoxia of previously unmentioned origin, pefinatal asphyxia, autoimmune disorders, metabolic and organ disorders which can be accompanied by damage to the brain, and also damage to the brain as a result of primary brain disorders, for example convulsive conditions and atero- and/or arteriosclerotic changes. For the treatment of chronic or psychiatric conditions such as, for example, depression, neurodegenerative disorders, such as, for example, Alzheimer's, Parkinson's or Huntington's disease, multiple sclerosis, amyotrophic lateral sclerosis, neurodegeneration due to acute and/or chronic viral or bacterial infections and multlinfarct dementia.

Moreover, they can be used as pharmaceuticals for the prevention and/or treatment of dementias of different origin, impaired brain performance owing to old age, memory disturbances, spinal injuries, states of pain, states of anxiety of different origin, medicament-related Parkinson's syndrome, psychoses (such as, for example, schizophrenia), brain oedma, neuronal damage after hypoglycaemia, emesis, nausea, obesity, addiction and withdrawal syndromes, CNS-mediated spasms, sedation and motor disturbances.

Furthermore, the compounds can be used for promoting neuronal regeneration in the post-acute phase of cerebral injuries or chronic disorders of the nervous system.

They are preferably employed as pharmaceuticals for the prevention and/or treatment of cerebral ischaemias, craniocerebral trauma, states of pain or CNS-mediated spasms (such as, for example, epilepsy).

The modulation of substances at the metabotropic glutamate receptor (direct or indirect effect on the coupling efficiency of the glutamate receptor to G-proteins) can be examined using primary cultures of granular cells from the cerebellum. Electrophysiological measurements on these cell cultures in the "cell attached" mode show that L-type $Ca^{2+}$-channels in this preparation are activated by mGluR1-glutamate receptors (J. Neurosci. 1995, 15, 135), whereas they are blocked by group II receptors (J. Neurosci. 1994, 14, 7067). By appropriate experimental arrangement, it is possible to monitor the modulatory effect of pharmacological test substances on glutamate receptors. Detailed examination of subtype specificity under controlled conditions can be carried out by injecting the appropriate mGluR subtype DNA into Xenopus oocytes (WO 92/10583).

Using the test models below, it is possible to demonstrate the antiischaemic activity of the compounds in vivo.
Permanent Focal Cerebral Ischaeiia in the Rat (MCA-O)

Under isoflurane anaesthesia, the medium cerebral artery is exposed on one side and the latter and its side branches are irreversibly sealed by means of electrocoagulation. As a result of the intervention the cerebral infarct is formed. During the operation, the body temperature of the animal is kept at 37° C. After wound closure and wearing off of the anaesthesia, the animals are again released into their cage. The administration of the substance is carried out according to different time schemes and via different administration routes (i.v. i.p.) after occlusion. The infarct size is determined after 7 days. To do this, the brain is removed, worked up histologically and the infarct volume is determined with the aid of a computer-assisted analysis system.
Subdural Haematona in the Rat (SDH)

Under anaesthesia, the animal's own blood is injected subdurally on one side. An infarct is formed under the haematoma. Substance administration is carried out according to different time schemes and via different administration routes (i.v. i.p.). The determination of the infarct size is carried out as described in the model of permanent focal ischaemia in the rat (MCA-O).

Using the method described in NeuroReport 1996, 7, 1469–1474, it is possible to test for antiepileptic activity.

The suitability of the compounds according to the invention for treating schizophrenia can be determined by the methods described in Science 1998, 281, 1349–1352 and Eur. J. Pharmacol. 1996, 316, 129–136.

The present invention includes pharmaceutical preparations which, in addition to inert, non-toxic, pharmaceutically suitable auxiliaries and excipients, comprise one or more compounds of the general formulae (I), (Ia) and (Ib) or which consist of one or more active compounds of the formulae (I), (Ia) and (Ib) and processes for producing these preparations.

In these preparations, the active compounds of the formulae (I), (Ia) and (Ib) should be present in a concentration of from 0.1 to 99.5% by weight, preferably from 0.5 to 95% by weight, of the total mixture.

In addition to the active compounds of the formulae (I), (Ia) and (Ib) the pharmaceutical preparations may also comprise other pharmaceutically active compounds.

The abovementioned pharmaceutical preparations can be prepared in a customary manner by known methods, for example with the auxiliary(s) or excipient(s).

In general, it has proved advantageous to administer the active compound(s) of the formulae (I), (Ia) and (Ib) in total amounts of about 0.01 to about 100 mg/kg, preferably in total amounts of about 1 mg/kg to 50 mg/kg, of body weight per 24 hours, if appropriate in the form of a plurality of individual administrations, to achieve the desired result.

However, if appropriate, it may be advantageous to depart from the amounts mentioned, namely depending on the type and on the body weight of the object treated, on the individual response towards the medicament, the nature and severity of the disorder, the manner of formulation and administration, and the time or interval at which administration takes place.

General Section

Mobile Phases for Chromatography

I Dichloromethane/methanol

II Dichloromethane/ethanol

III Cyclohexane/ethyl acetate

IV Cyclohexane/dichloromethane

V Butyl acetate (200), butanol (26), acetic acid (100), phosphate buffer pH=6 (60)

Abbreviations

DME- 1,2-Dimethoxyethane

HMPA- Hexamethylphosphoric triamide

LiHMDS- Lithium bistrimethylsilylamide

LDA- Lithium diisopropylamide

MTBE- Methyl tert-butyl ether

THF Tetrahydrofuran

STARTING MATERIALS

Example 1A

Hexahydro-benzofuran-2-one

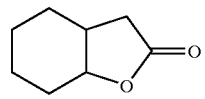

2-Oxocyclohexylacetic acid (31.2 g, 200 mmol) is dissolved in 125 ml of 0.2 N aqueous sodium hydroxide solution and, at room temperature, added dropwise to a solution of sodium borohydride (18.9 g, 500 mmol) in 150 ml of 0.2 N aqueous sodium hydroxide solution. The mixture is stirred for 20 h and then cooled to 0° C. and carefully acidified with 6 N HCl. The strongly acidic solution is then heated at 100° C. for 30 min and subsequently stirred overnight. The cold mixture is then extracted with MTBE, and the combined ether phases are washed with 5% strength sodium carbonate solution and sat. NaCl solution, dried over magnesium sulphate, filtered and concentrated. Purification is carried out by distillation (b.p.: 75° C./0.01 mm). Yield: 22.9 g (81.7%). MS (CI): m/e=141 [M+H$^+$]

PREPARATION EXAMPLES

Examples 1, 2 and 3

3-(Naphth-2-ylmethyl)-hexahydro-cyclopenta[b]furan-2-one

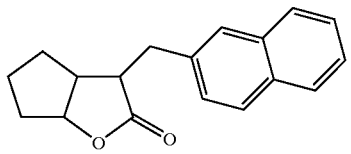

Under argon, 8.7 ml of a 1 molar solution of lithium bis-(trimethylsilyl)-amide in THF are added dropwise to a solution, cooled to −78° C., of 1 g (7.9 mmol) of hexahydro-cyclopenta[b]furan-2-one in 20 ml of THF such that the temp. of the mixture does not exceed −65° C. After the addition has ended, stirring is continued at −78° C. for 10 min, and 1.93 g (8.7 mmol) of naphth-2-ylmethyl bromide are then added in one portion. Immediately afterwards, the cooling bath is removed and the mixture is allowed to warm to room temp. After 16 h of stirring at room temp., the mixture is taken up in water/diethyl ether and the aqueous phase is extracted twice with diethyl ether. The combined organic phases are dried over sodium sulphate and then concentrated. The residue is chromatographed over silica gel (mobile phase: dichloromethane); Yield: 1.2 g, colourless oil, diastereomer mixture: 87:13 (Example 1) $^1$H-NMR (200 MHz; [d$_6$]-DMSO): δ[ppm]=1.2–1.9 (br m,7H), 2.6 (m,1H), 2.87 (dd, 1H); 2.93 (dd,1H), 4.72/4.75 (m;1H), 7.48–7.55 (m;3H), 7.76 (s;1H), 7.81–7.95 (m;3H).

The diastereomers and enantiomers are separated using preparative HFPLC (Rainin C18, acetonitrile/H$_2$O 55:45).

Example 2 (fraction 1, diastereomer A) and Example 3 (fraction 2, diastereomer B).

Example 4

(3R*,3aR*,6aS*)-3-Allyl-3-(naphth-2-ylmethyl)-hexahydrocyclopenta[b]furan-2-one

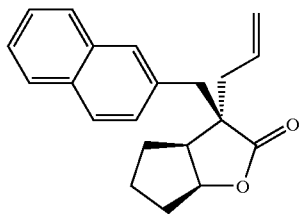

Under argon, 1.9 ml of a 1 molar solution of lithium bis-(trimethylsilyl)-amide in THF are added dropwise to a solution, cooled to −78° C., of 0.5 g (1.88 mmol) of the compound from Example 1 in 20 ml of THF such that the temp. of the mixture does not exceed −65° C. After the addition has ended, stirring is continued at −78° C. for 10 min, and 0.26 g (2.25 mmol) of allyl bromide are then added in one portion. Immediately afterwards, the cooling bath is removed and the mixture is allowed to warm to room temp. After 16 h of stirring at room temp., the mixture is taken up in ammonium chloride solution and ethyl acetate and the aqueous phase is extracted twice with ethyl acetate. The combined organic phases are dried over sodium sulphate and then concentrated. The residue was chromatographed over silica gel (mobile phase: dichloromethane). Yield: 255 mg (44%) of a colourless oil. $^1$H-NMR (200 MHz; CDCl$_3$) δ[ppm]=1.55–2.2 (br m,6H), 2.3 (m, 2H), 2.61 (m,1H), 3.12 (d,1H), 3.3 (d,1H), 4.91 (m,1H), 5.05 (dd,1H), 5.11 (dd, 1H), 5.8 (ddt,1H), 7.35–7.5 (br m,3H), 7.72 (s,1H), 7.80 (m,3H). Diastereomeric purity: >99% de (HPLC).

Example 5

3-Allyl-hexahydro-cyclopenta[b]furan-2-one

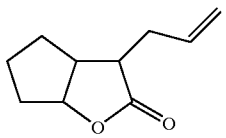

Analogously to the procedure of Example 1, the title compound is was prepared from 1.2 g (9.5 nmuol) of hexahydro-cyclopenta[b]furan-2-one, 10 ml of 1 molar lithium bis-(trimethylsilyl)-amide solution in THF and 1.29 g (9.5 mmol) of allyl bromide in 20 ml of THF. Yield: 1.25 g (79%) of a colourless oil. $^1$H-NMR(200 MHz; [d$_6$]-DMSO): δ[ppm]: 1.47–1.89 (br m,6H), 2.15–2.55 (br m,4H), 4.41 (m,1H), 5.12 (dd,1H), 5.18 (dd,1H), 5.76 (ddt, 1H)

Example 6

(3S*,3aR*,6aS*)-3-Allyl-3-(naphth-2-ylmethyl)hexahydro-cyclopenta[b]furan-2-one

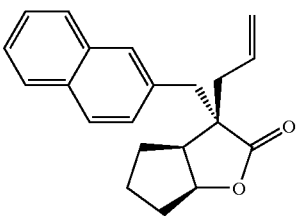

Analogously to the procedure of Example 4, the title compound is prepared from 0.55 g (3.3 mmol) of the compound from Example 3, 4 ml of 1 molar lithium bis-(trimethylsilyl)-amide solution in THF and 0.73 g (3.3 mmol) of 2-(bromomethyl)-naphthalcne in 15 ml of THF. Yield: 823 mg (81.2%) of a colourless oil. $^1$H-NMR (200 MHz; CDCl$_3$): δ[ppm]: 1.4–1.85 (br m,6H), 2.47 (ddt,1H), 2.61 (br m,2H), 3.01 (d,1H), 3.11 (d,1H), 3.62 (m,1H), 5.25 (dd,1H), 5.29 (dd,1H), 5.96 (ddt,1H), 7.33 (dd,1H), 7.48 (m,2H), 7.67 (s,1H), 7.73–7.86 (br m,3H) Diastereomeric purity: >99% de (HPLC)

Examples 7, 8, 9, 10 and 11

3-(Naphth-2-ylmethyl)- 3,3a,6,6a-tetrahydro-cyclopenta[b]furan-2-one

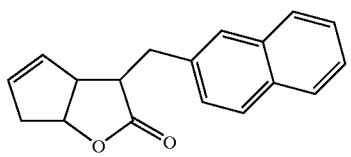

Analogously to the procedure of Example 1, the title compound was prepared from 7.4 g (59.6 mmol) of 3,3a,6,6a-tetrahydro-cyclopenta[b]furan-2-one, 60 ml of a 1 molar lithium bis-(trimethylsilyl)-amide solution in THF and 13.2 g (59.7 mmol) of 2-(bromomethyl)-naphthalene in 180 ml of THF. Chromatographic purification is carried out using a mixture of dichloromethane and petroleum ether (40–60) in a ratio of 100:4. Yield: 10.6 g (67.3%), pale yellow oil, diastereomeric mixture: 2.5:1 (Example 7). MS (ESI)[m/e]: 287 [M+Na$^+$]

Separation into the diastereomers and enantiomers is carried out using preparative HPLC (Daicel Chiralpak AD, heptane/ethanol 9:1): This gives Examples 8, 9, 10 and 11.

Example 8 (fraction 1)
Example 9 (fraction 2)
Example 10 (fraction 3)
Example 11 (fraction 4)

The compounds listed in Table 1 below were prepared analogously to the procedures of Examples 1–7.

TABLE 1

| Ex. No. | Structure | Yield (% of theory) | MS |
|---|---|---|---|
| 12 | 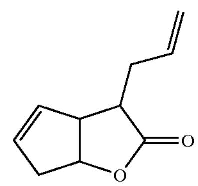 | 43 | 182 (M + NH$_4^+$) |
| 13 | 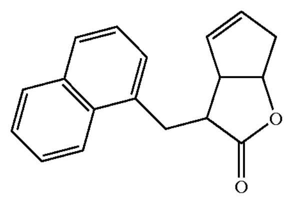 | 35 | 306 (M + H$_3$CCN + H$^+$) |
| 14 | 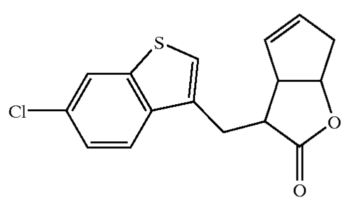 | 47 | 256 (M + H$_3$CCN + H$^+$) |
| 15 | 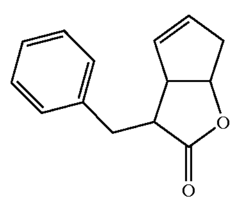 | 75 | 256 (M + H$_3$CCN + H$^+$) |
| 16 | 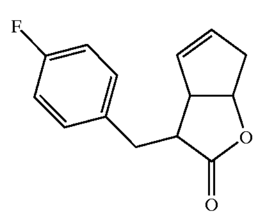 | 73 | 274 (M + H$_3$CCN + H$^+$) |

TABLE 1-continued

| Ex. No. | Structure | Yield (% of theory) | MS |
|---|---|---|---|
| 17 | 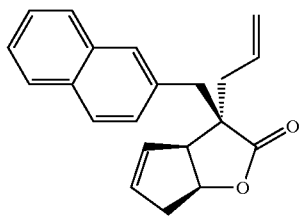 | 68 | 274 (M + H₃CCN + H⁺) |
| 18 | 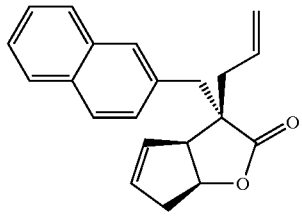 | 61 | 274 (M + H₃CCN + H⁺) |

Example 19

(3R*,3aR*,6aS*)-3-Allyl-3-(naphth-2-ylmethyl)-3,3a,6,6a-tetrahydrocyclopenta[b]furan-2-one Analogously to the procedure of Example 3, the title compound was prepared from 0.79 g (3 mmol) of the compound from Example 7, 3 ml of 1 molar lithium bis (trimethylsilyl)-amide solution in THF and 0.36 g (3 mmol) of allyl bromide in 10 ml of THF. Chromatographic purification was carried out using a mixture of dichloromethane and petroleum ether (40–60) in a ratio of 100:4. Yield: 684 mg (74.8%) of a pale yellow oil; Diastereomeric purity: >99% de (HPLC). MS (DCI/NH₃) [m/e]: 322 (100, M+NH₄⁺) $^1$H-NMR (200 MHz; CDCl₃): δ[ppm]=2.24 (dd, 1H); 2.37 (dd,1H), 2.72 (m,2H), 3.16 (d,1H), 3.28 (d,1H), 3.48(m,1H), 5.03 (dd,1H), 5.05 (m,1H), 5.12 (dd,1H), 5.78 (ddt,1H), 5.89 (m,1H), 6.04 (m,1H), 7.4–7.5 (br m,3H), 7.75 (s,1H), 7.8 (m,3H)

Example 20

(3R*,3aR*,6aS*)-3-Allyl-3-(naphth-2-ylmethyl)-3,3a,6,6a-tetrahydrocyclopenta[b]furan-2-one Analogously to the procedure of Example 3, the title compound was prepared from 0.42 g (2.56 mmol) of the compound from Example 12, 2.6 ml of 1 molar lithium bis-(trimethylsilyl)-amide solution in THF and 0.57 g (2.56 mmol) of 2-bromomethylnaphthalene in 5 ml of THF. Chromatographic purification was carried out using a mixture of dichloromethane and petroleum ether (40–60) in a ratio of 100:4. Yield: 487 mg (62.6%) of a pale yellow oil. Diastereomeric purity: >99% de (HPLC). MS (DCI/NH₃)[m/e]: 322 (100, M+NH₄⁺) $^1$H-NMR (200 MHz; CDCl₃): δ[ppm]= 2.42 (m,2H), 2.45 (dd,1H), 2.67 (dd,1H), 3.03 (d,1H), 3.15 (d,1H), 3.51(m,1H), 3.53 (m,H), 5.31 (dd, 1H), 5.33 (dd, 1H), 5.72 (m,H), 6.03 (ddt,H), 7.36 (dd,1), 7.48 (m,2H), 7.69 (s,1H), 7.75–7.88 (br m,3H)

Examples 21, 22, 23, 24 and 25

3-(Naphth-2-ylmethyl)-3,3a,4,6a-tetrahydro-cyclopenta[b]furan-2-one

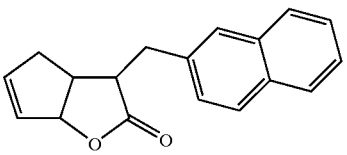

Analogously to the procedure of Example 1, the title compound was prepared from 0.31 g (2.5 mmol) of 3,3a,4,6a-tetrahydro-cyclopenta[b]furan-2-one, 2.5 ml of a 1 molar lithium bis-(trimethylsilyl)-amide solution in THF and 0.55 g (2.5 mmol) of 2-(bromomethyl)-naphthalene in 10 ml of THF. Yield: 498 mg (75.4%) of a pale yellow oil (Example 21). Diastereomer mixture: 94:6 (HPLC) MS (EI): m/e=264 [M⁺] The separation into the diastereomers and enantiomers is carried out using preparative HPLC: Example 22, 23, 24 and 25.

Example 26

3-Allyl-3,3a,4,6a-tetrahydro-cyclopenta[b]furan-2-one

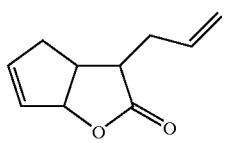

Analogously to the procedures of Example 1, the title compound was prepared from 0.31 g (2.5 mmol) of 3,3a,4,6a-tetrahydro-cyclopenta[b]furan-2-one, 2.5 ml of a 1 molar lithium bis-(trimethylsilyl)-amide solution in THF and 0.36 g (2.5 mmol) of allyl bromide in 7 ml of THF. Yield: 278 mg (67.8%) of a colourless oil. MS (DCI/NH$_3$): m/e=182 [M+NH$_4^+$]

Example 27

(3R*,3aR*,6aS*)-3-Allyl-3-(naphth-2-ylmethyl)-3,3a,4,6a-tetrahydrocyclopenta[b]furan-2-one

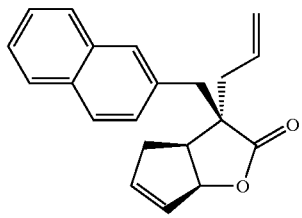

Analogously to the procedure of Example 4, the title compound was prepared from 0.4 g (1.5 mmol) of the compound from Example 15, 1.5 ml of 1 molar lithium bis-(trimethylsilyl)-amide solution in THF and 0.22 g (1.8 mmol) of allyl bromide in 10 ml of THF. Yield: 198 mg (43.2%) of a pale yellow oil. Diastereomeric purity: 72% de (HPLC). MS (DCI/NH$_3$): m/e=322 [M+NH$_4^+$] $^1$H-NMR (200 MHz; CDCl$_3$): δ[ppm]: 2.29 (dd;1H), 2.41 (dd;1H), 2.79 (m;2H), 2.85 (m;1H), 3.14 (d;1H), 3.34(d;1H), 5.09 (dd; 1H), 5.16 (dd;1H), 5.31 (m;1H), 5.82 (ddt;1H), 5.92 (m;1H), 6.22 (m;1H), 7.48 (dd;1H), 7.49 (m;2H), 7.7 (s;1H), 7.8 (m;3H)

Example 28

(3R*,3aR*,6aS*)-3-Ally-3-(naphth-2-ylmethyl )-3,3a,4,6a-tetrahydrocyclopenta[b]furan-2-one

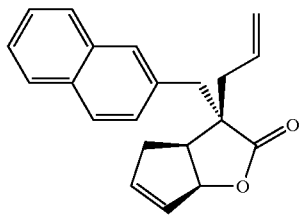

Analogously to the procedure of Example 4, the title compound was prepared from 0.23 g (1.38 mmol) of the compound from Example 16, 1.4 ml of 1 molar lithium bis-(trimethylsilyl)-amide solution in THF and 0.3 g (1.38 mmol) of 2-bromomethylnaphthalene in 5 ml of THF. Yield: 259 mg (61.8%) of a pale yellow oil. Diastereomeric purity: >99% de (HPLC). $^1$H-NMR (200 MHz; CDCl$_3$): δ[ppm]: 2.62 (m;4H), 2.95 (dd;1H), 3.5 (d;1H), 3.17(d;1H), 4.11 (m;1H), 5.28 (m;2H), 5.53 (m;1H), 5.96 (ddt;2H), 6.07 (m;1H), 7.36 (dd;1H), 7.49 (m;2H), 7.60 (s;1H), 7.78–7.88 (br m;3H)

Example 29 and Example 30

8-Naph-2-yl-methyl-2,3-epoxy-6-oxabicyclo[3.3.0]octan-7-one

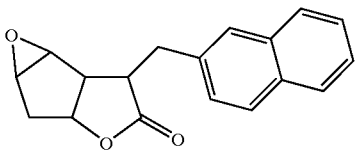

1.3 g (4.92 mmol) of the compound from Example 7 and 2 g (10 mmol) of m-chloroperbenzoic acid in 50 ml of chloroform were boiled under reflux for 4 h. After cooling to room temperature, the mixture was washed with sodium hydrogen sulphite solution and with sat. sodium carbonate solution, and the organic phase was dried over sodium sulphate and then concentrated. The residue was chromatographed over silica gel (mobile phase: dichloromethane/methanol (100:0.5). Yield: two diastereomer mixtures (Example 29 (315 mg; 22.8%) and Example 30 (409 mg; 29%) which contain the epimeric epoxides in about 1:1. Example 29: MS (ESI): m/e=281[M+H] Example 30: MS (ESI) m/e=281 [M+H]

Example 31

4,5-Dihydroxy-3-(naphth-2-ylmethyl)-hexahydro-cyclopenta[b]furan-2-one

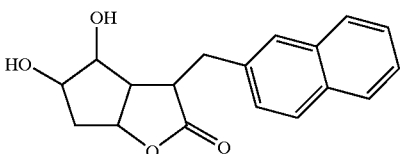

200 mg (0.75 mmol) of the compound from Example 7, 0.08 ml of a 2.5% strength osmium tetroxide solution in tert-butanol and 180 mg of N-methylmorpholine N-oxide were dissolved in 2.5 ml of acetone and stirred at RT for 15 h. The mixture was concentrated and the residue was chromatographed over silica gel (mobile phase: dichloromethane/methanol (100:4)). Yield: 161 mg of a diastereomer mixture. Diastereomer ratio: 1:5:5:1 (HPLC). MS (DCI/NH$_3$): m/e=316 (M+NH$_4$)

Example 32

3-(2-Naphthylmethyl)-hexahydro-benzofuran-2-one

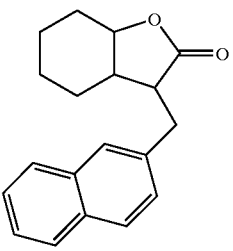

Under argon, a solution of diisopropylamine (3.36 ml, 24 mmol) in 20 ml of dry THF was cooled to 0° C. and admixed with butyllithium (9.6 ml, 24 mmol, 2.5 M in hexane). The solution was stirred with ice-cooling for 15 min, cooled to −78° C. and admixed with a solution of hexahydro-benzofuran-2-one (2.8 g, 20 mmol) in 10 ml of THF. This mixture was stirred at −78° C. for 1 h, and a solution of 2-bromomethylnaphthalene (5.31 g, 24 mmol) in 20 ml of THF was then added. The mixture was stirred at −78° C. for another 2 h and then at room temperature overnight. Water was then added, the organic solvent was removed under reduced pressure and the aqueous phase was extracted with MTBE. The combined ether phases were dried over magnesium sulphate, filtered and concentrated. Purification was carried out by column chromatography. Yield: 2.5 g (44.6%). $R_f$ (cyclohexane/ethyl acetate 3:1)=0.69, $R_f$ (cyclohexane/ethyl acetate 1:1)=0.83 MS (CI): m/e=281 [M+H$^+$]

What is claimed is:

1. Compounds of the general formula (I)

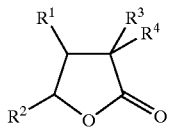
(I)

in which $R^1$ and $R_2$ together represent radicals of the formulae

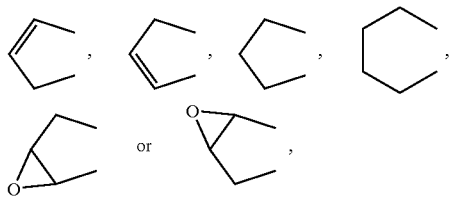

which are optionally substituted up to 3 times by hydroxyl, $R^3$ represents hydrogen, $(C_1-C_6)$-alkyl or represents $(C_2-C_6)$alkenyl and $R^4$ represents a radical of the formula –CH$_2$—R$^5$, in which $R^5$ represents aryl having 6 to 10 carbon atoms or benzothiophene which is attached via the heterocycle, where the ring systems are optionally mono- to polysubstituted by identical or different substituents from the group consisting of halogen and $(C_1-C_6)$-alkyl, or $R^3$ represents $(C_3-C_5)$-alkenyl and $R^4$ represents hydrogen;

and their pharmaceutically acceptable salts.

2. Compounds of the formula (I) according to claim 1, in which $R^1$ and $R^2$ together represent radicals of the formulae

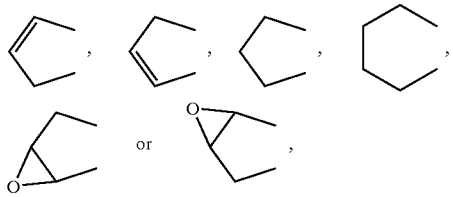

which are optionally substituted up to 3 times by hydroxyl, $R^3$ represents hydrogen or represents $(C_2-C_5)$-alkenyl and $R^4$ represents a radical of the formula —CH$_2$—R$^5$, in which $R^5$ represents phenyl, naphthyl or benzothiophene which is attached via the heterocycle, where the ring systems are optionally mono- to polysubstituted by identical or different substituents from the group consisting of fluorine, chlorine, bromine and $(C_1-C_4)$-alkyl, or $R^3$ represents $(C_3-C_5)$-alkenyl and $R^4$ represents hydrogen;

and their pharmaceutically acceptable salts.

3. Compounds of the formula (I) according to claim 1 or 2, in which $R^1$ and $R^2$ together represent radicals of the formulae

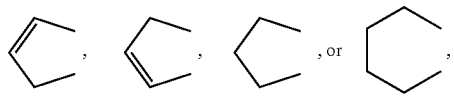

which are optionally substituted up to 2 times by hydroxyl, $R^3$ represents hydrogen or represents $(C_3-C_5)$-alkenyl and $R^4$ represents a radical of the formula —CH$_2$—R$^5$, in which $R^5$ represents phenyl, naphthyl or benzothiophene which is attached via the heterocycle, where the ring systems are optionally momo- to disubstituted by identical or different substituents from the group consisting of fluorine, chlorine, bromine and $(C_1-C_3)$-alkyl, or $R^3$ represents $(C_3-C_5)$-alkenyl and $R^4$ represents hydrogen;

and their salts.

4. A process for preparing the compounds of the formula (I)

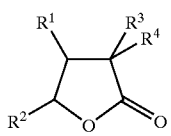 (I)

in which

R¹ and R² together represent radicals of the formulae

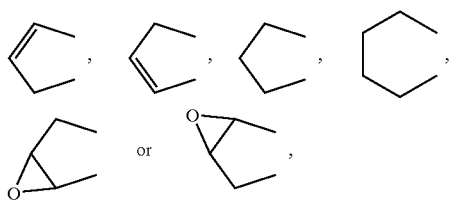

which are optionally substituted up to 3 times by hydroxyl,

R³ represents hydrogen, $(C_1-C_6)$-alkyl or represents $(C_2-C_6)$alkenyl and

R⁴ represents a radical of the formula $—CH_2—R^5$, in which

R⁵ represents aryl having 6 to 10 carbon atoms or benzothiophene which is attached via the heterocycle, where the ring systems are optionally mono- to polysubstituted by identical or different substituents from the group consisting of halogen and $(C_1-C_6)$-alkyl, or R³ represents $(C_3-C_5)$-alkenyl and R⁴ represents hydrogen;

comprising:

(a) reacting a compound of the general formula (II),

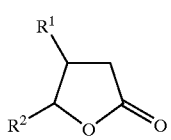 (II)

in which

R¹ and R² are as defined above, with a compound of the general formula (II)

R⁴—A (III)

in which

R⁴ is a radical $—CH_2—R^5$ as defined above, and

A represents halogen in an inert solvent and in the presence of base to give a compound of the general formula (Ia)

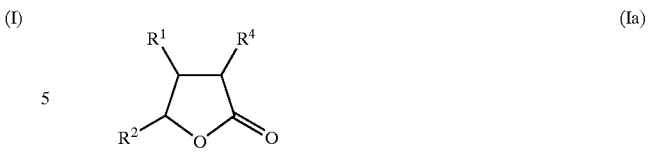 (Ia)

and, in the case that R³ of formula (I) does not represent hydrogen, reacting the compound of the general formula (Ia) with a compound of the general formula (IV)

R³'—D (IV)

in which

R³' represents $(C_1-C_6)$-alkyl or $(C_2-C_6)$-alkenyl and

D represents halogen, in an inert solvent and in the presence of base, to yield a compound of general formula (I), or (b) initially reacting a compound of the general formula (II) with a compound of the general formula (IV) as described under (a) above to give the compound of the general formula (Ib)

 (Ib)

in which

R¹, R² and R³' are as defined above, followed by reaction of the compound of general formula (Ib) with a compound of the general formula (III) to yield a compound of general formula (I).

5. A pharmaceutical composition, comprising, as an active component, at least one compound according to claim 1 in admixture with at least one pharmaceutically acceptable, essentially non-toxic carrier or excipient.

6. A compound according to claim 1, selected from the group consisting of:
   3-allyl-3-(naphth-2-ylmethyl)hexahydro-cyclopenta(b) furan-2-one;
   3-(naphth-2-ylmethyl)-3,3a,6,6a-tetrahydro-cyclopenta (b)furan-2-one; and
   3-(naphth-2-ylmethyl)-3,3a,4,6a-tetrahydro-cyclopent(b) furan-2-one.

7. The process of claim 4, wherein A is bromine.

8. The process of claim 4, wherein D is bromine.

9. A method of treating disorders caused by hyper- or hypofunction of the glutamatergic system, comprising administering to a patient in need thereof an effective amount of a compound according to claim 1.

10. A method of treating cerebral ischaemias, craniocerebral trauma, states of pain or CNS-mediated spasms, comprising administering to a patient in need thereof an effective amount of a compound according to claim 1.

* * * * *